(12) United States Patent
Kirschman

(10) Patent No.: US 7,922,747 B2
(45) Date of Patent: Apr. 12, 2011

(54) CROSS CONNECTOR APPARATUS FOR SPINAL FIXATION RODS

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 739 days.

(21) Appl. No.: 11/873,452

(22) Filed: Oct. 17, 2007

(65) Prior Publication Data

US 2009/0105763 A1 Apr. 23, 2009

(51) Int. Cl.
*A61B 17/88* (2006.01)
(52) U.S. Cl. ....................................................... 606/251
(58) Field of Classification Search ........... 606/246–279
See application file for complete search history.

(56) References Cited

U.S. PATENT DOCUMENTS

| | | |
|---|---|---|
| 3,648,691 A | 3/1972 | Lumb et al. |
| 4,085,744 A | 4/1978 | Lewis et al. |
| 4,269,178 A | 5/1981 | Keene |
| 4,289,124 A | 9/1981 | Zickel |
| 4,411,259 A | 10/1983 | Drummond |
| 4,604,995 A | 8/1986 | Stephens et al. |
| 4,611,580 A | 9/1986 | Wu |
| 4,611,581 A | 9/1986 | Steffee |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,719,905 A | 1/1988 | Steffee |
| 4,771,767 A | 9/1988 | Steffee |
| 4,815,453 A | 3/1989 | Cotrel |
| 4,887,595 A | 12/1989 | Heinig et al. |
| 4,887,596 A | 12/1989 | Sherman |
| 4,913,134 A | 4/1990 | Luque |
| 4,946,458 A | 8/1990 | Harms et al. |
| 5,005,562 A | 4/1991 | Cotrel |
| 5,024,213 A | 6/1991 | Asher et al. |
| 5,042,982 A | 8/1991 | Harms et al. |
| 5,067,955 A | 11/1991 | Cotrel |
| 5,084,049 A | 1/1992 | Asher et al. |
| 5,092,867 A | 3/1992 | Harms et al. |
| 5,129,900 A | 7/1992 | Asher et al. |
| 5,176,680 A | 1/1993 | Vignaud et al. |
| 5,190,543 A | 3/1993 | Schlapfer |

(Continued)

FOREIGN PATENT DOCUMENTS

DE 3639810 A1 5/1988

*Primary Examiner* — Eduardo C Robert
*Assistant Examiner* — Summer L Kostelnik
(74) *Attorney, Agent, or Firm* — Jacox, Meckstroth & Jenkins

(57) ABSTRACT

A cross connector apparatus for retaining a pair of spinal rods in spaced relation, including: a middle portion having a first end, a second end, and an extendable member which is able to extend beyond the second end a specified amount; a first side portion positioned adjacent to the first end of the middle portion, wherein the first side portion is rotatably coupled to the middle portion in at least a first plane; and, a second side portion positioned adjacent to the second end of the middle portion, wherein the second side portion is rotatably coupled to the extendable member in at least a second plane. The first and second side portions each further include a mechanism for both retaining the respective side portion in a desired position with respect to the middle portion and retaining a spinal rod member to the respective side portion.

20 Claims, 5 Drawing Sheets

U.S. PATENT DOCUMENTS

| | | |
|---|---|---|
| 5,207,678 A | 5/1993 | Harms et al. |
| 5,257,993 A | 11/1993 | Asher et al. |
| 5,624,442 A | 4/1997 | Mellinger et al. |
| 5,947,966 A | 9/1999 | Drewry et al. |
| 6,136,003 A | 10/2000 | Hoeck et al. |
| 6,234,705 B1 | 5/2001 | Troxell |
| 6,264,658 B1 | 7/2001 | Lee et al. |
| 6,283,967 B1 | 9/2001 | Troxell et al. |
| 6,306,137 B2 | 10/2001 | Troxell |
| 6,309,391 B1 | 10/2001 | Crandall et al. |
| 6,413,258 B1 | 7/2002 | Bernhardt, Jr. |
| 6,626,904 B1 | 9/2003 | Jammet et al. |
| 6,736,817 B2 | 5/2004 | Troxell et al. |
| 6,872,208 B1 | 3/2005 | McBride et al. |
| 6,887,241 B1 | 5/2005 | McBride et al. |
| 6,958,066 B2 | 10/2005 | Richelsoph et al. |
| 2001/0047171 A1 | 11/2001 | Troxell et al. |
| 2002/0007183 A1 | 1/2002 | Lee et al. |
| 2002/0120272 A1 | 8/2002 | Yuan et al. |
| 2003/0105460 A1 | 6/2003 | Crandall et al. |
| 2003/0212398 A1* | 11/2003 | Jackson .......................... 606/61 |
| 2004/0039385 A1 | 2/2004 | Mazda et al. |
| 2004/0133203 A1 | 7/2004 | Young et al. |
| 2004/0176765 A1 | 9/2004 | Troxell et al. |
| 2005/0090821 A1* | 4/2005 | Berrevoets et al. ............. 606/61 |
| 2006/0064093 A1 | 3/2006 | Thramann et al. |
| 2006/0195086 A1 | 8/2006 | Sybert |

* cited by examiner

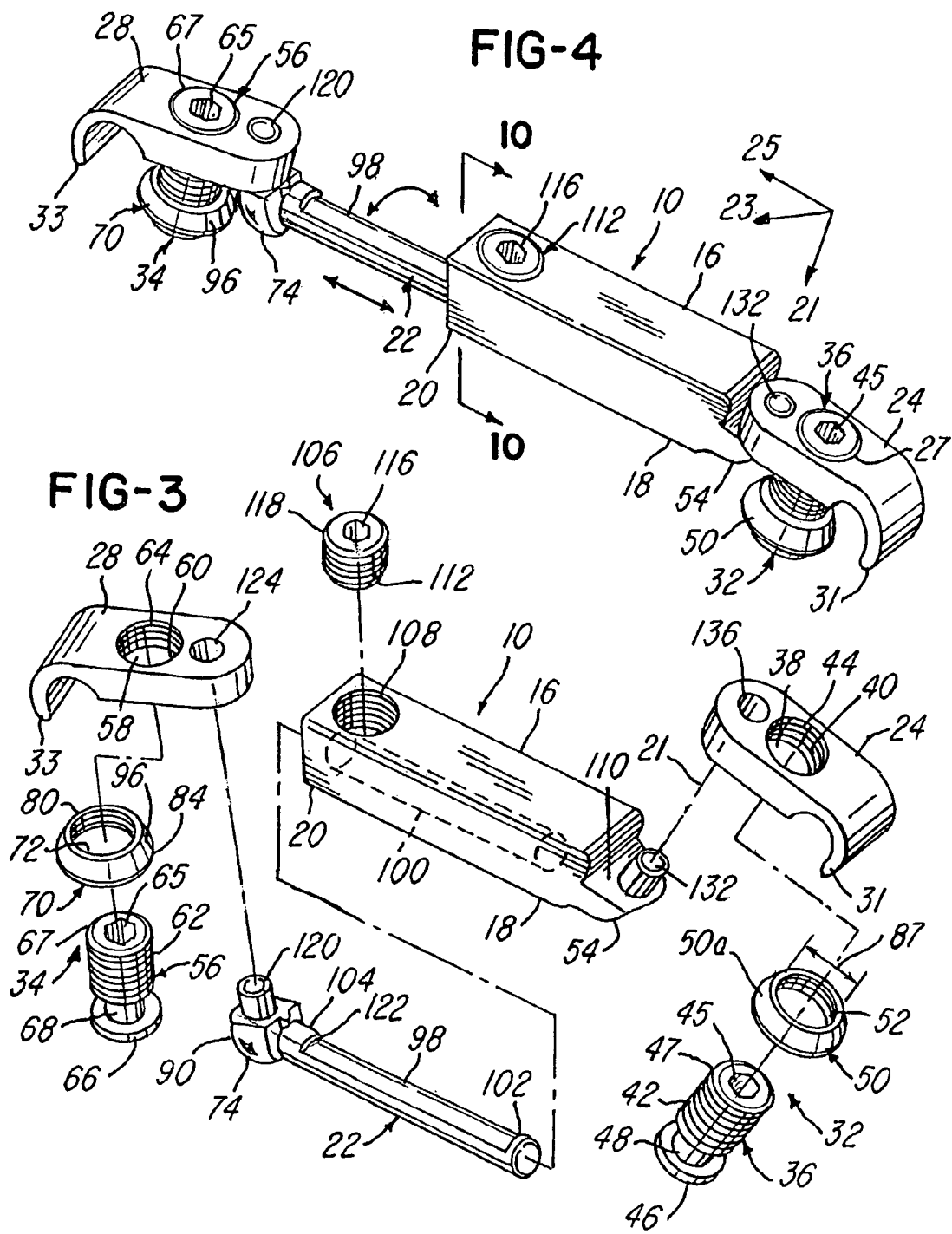

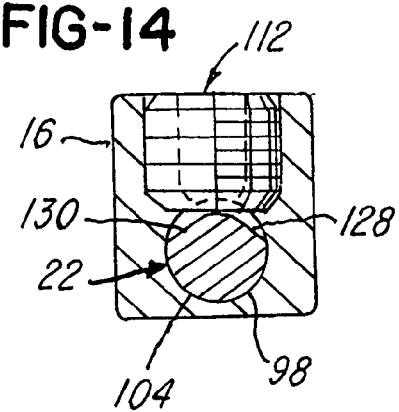
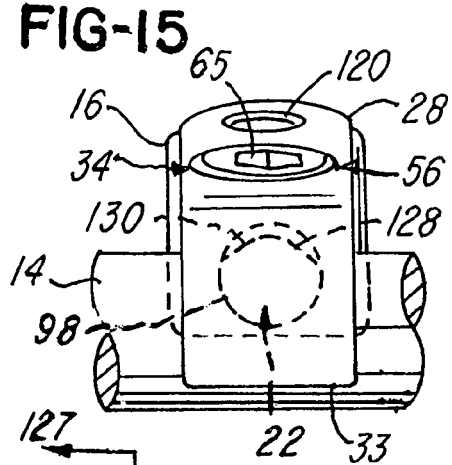
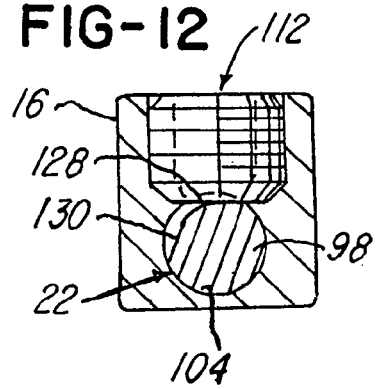
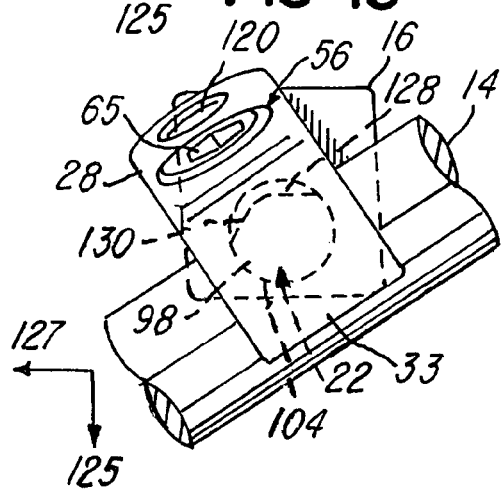
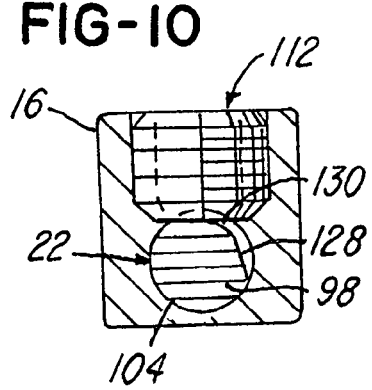
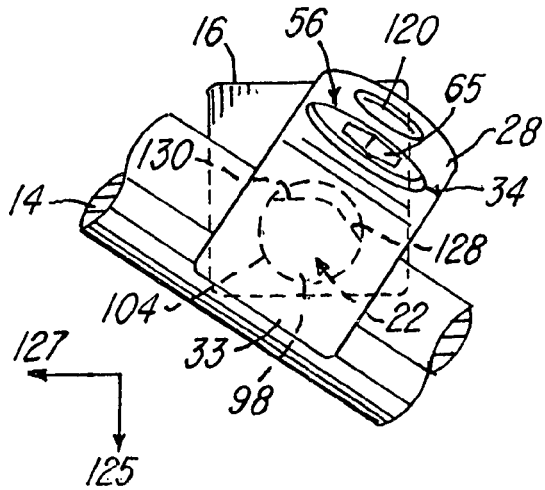

CROSS CONNECTOR APPARATUS FOR SPINAL FIXATION RODS

BACKGROUND OF THE INVENTION

1. Field of the Invention

The present invention relates generally to a cross connector for use in coupling spinal rods in a spinal fixation system and, in particular, to the manner of retaining and adjusting such spinal rods with respect thereto.

2. Description of the Related Art

As is generally known in the art, spinal abnormalities may be correctable using a pair of posterior spinal fixation rods attached to the vertebrae using pedicle screws and the like. In order to provide increased stability and rigidity, especially to resist twisting or the like, the pair of elongated rods often include cross connecting devices. The cross connecting devices typically traverse the spinal column and couple to each of the elongated rods. In other words, the cross connecting devices are perpendicular or substantially perpendicular to the spinal column.

One difficulty with connecting the elongated rods using such cross connecting devices resides in the fact that the pair of elongated rods is not exactly parallel and equally spaced along the spine. The cross connecting devices typically include at least two separate portions that couple together to compensate for these deviations. In order to accommodate the relative positions of the elongated rods, the cross connecting devices must be adjustable rotationally, angularly, and vertically. This typically involves adjusting and re-adjusting the various components of the cross connecting device related to the positioning thereof, which necessarily involves a trial and error approach. While this may be unavoidable, the constant need to loosen and tighten the locking or retaining mechanisms associated with such adjustments increases the time required to complete the operation.

Another difficulty encountered by cross connecting devices is the manner in which such devices are retained to the elongated rods. Some rod fasteners of cross connecting devices use threaded fasteners, such as a set screw or a nut, to attach the device to the adjacent rods. Such a threaded fastener must be tightened enough to prevent movement, but not be over tightened to the point that it causes damage to the rod. Certain configurations have also been disclosed to avoid potential damage created by point contact with the rods. Exemplary configurations are disclosed in U.S. Pat. No. 5,947,966 to Drewry et al., U.S. Pat. No. 6,136,003 to Hoeck et al., U.S. Pat. No. 6,283,967 to Troxell et al., U.S. Pat. No. 6,872,208 to McBride et al., U.S. Pat. No. 6,887,241 to McBride et al., U.S. Pat. No. 6,958,066 to Richelsoph et al., and published U.S. application 2006/0064093 to Thramann et al.

Thus, it would be desirable for a cross connector apparatus to be developed for use with a spinal fixation system which minimizes the number of fasteners required for adjusting the position of the apparatus with respect to the spinal rods. It would also be desirable for a cross connector apparatus to utilize a more efficient mechanism of retaining the spinal rods thereto.

SUMMARY OF THE INVENTION

In accordance with a first exemplary embodiment of the invention, a cross connector apparatus for retaining a pair of spinal rods in spaced relation is disclosed as including: a middle portion having a first end, a second end, and an extendable member which is able to extend beyond the second end a specified amount; a first side portion positioned adjacent to the first end of the middle portion, wherein the first side portion is rotatably coupled to the middle portion in at least a first plane; and, a second side portion positioned adjacent to the second end of the middle portion, wherein the second side portion is rotatably coupled to the extendable member in at least a second plane. The first and second side portions each further include a mechanism for both retaining the respective side portion in a desired position with respect to the middle portion and retaining a spinal rod member to the respective side portion. The retaining mechanism of the first side portion further includes: a cylindrical member which is adjustably engagable with an opening through the first side portion; a first ring member affixed to a first end of the cylindrical member; and, a second ring member adjustably engagable with the cylindrical member, wherein the second ring member is able to move along the cylindrical member so as to interface with the first ring member. In this way, the cylindrical member is able to move into and out of the opening so that the second ring member engages and disengages the spinal rod member and a shoulder at the first end of the middle portion. The mechanism of the second side portion further includes: a cylindrical member adjustably engagable with an opening through the second side portion; a first ring member affixed to a first end of the cylindrical member; and, a second ring member adjustably engagable with the cylindrical member, wherein the second ring member is able to move along the cylindrical member so as to interface with the first ring member. In this way, the cylindrical member is able to move into and out of the opening so that the second ring member engages and disengages the spinal rod member and a shoulder of the extendable member.

In a second exemplary embodiment of the invention, a process for retaining a pair of spinal rods in spaced relation is disclosed as including the following steps: retaining a first spinal rod to a first side portion of a cross connector apparatus; retaining the first side portion of the cross connector apparatus in a desired position; moving a second side portion of the cross connector apparatus coupled to the first side portion a specified distance from the first side portion; retaining a second spinal rod to the second side portion of the cross connector apparatus; and, retaining the second side portion of the cross connector apparatus in a desired position. The first two retaining steps occur substantially simultaneously and the last two retaining steps occur substantially simultaneously.

BRIEF DESCRIPTION OF THE DRAWINGS

FIG. 3 is an exploded perspective view of the cross connector apparatus depicted in FIGS. 1 and 2;

FIG. 4 is a perspective view of the cross connector apparatus depicted in FIGS. 1-3, where one of the side portions is in an extended position;

FIG. 10 is a section view of the cross connector apparatus depicted in FIGS. 1-8 taken along line 10-10 in FIG. 4, where an extendable member has been rotated clockwise in a vertical plane with respect to a middle portion thereof;

FIG. 11 is a partial side view of the cross connector apparatus depicted in FIG. 10, where the side portion has been rotated clockwise in a vertical plane with respect to a middle portion thereof;

FIG. 12 is a section view of the cross connector apparatus similar to that depicted in FIG. 10, where an extendable member has been rotated counter-clockwise in a vertical plane with respect to a middle portion thereof;

FIG. 13 is a partial side view of the cross connector apparatus depicted in FIG. 12, where the side portion has been rotated counter-clockwise in a vertical plane with respect to a middle portion thereof;

FIG. 14 is a section view of the cross connector apparatus similar to that depicted in FIG. 10, where an extendable member is in a neutral position with respect to the middle portion thereof; and FIG. 15 is a partial side view of the cross connector apparatus depicted in FIG. 14, where the side portion is aligned with the middle portion thereof.

DETAILED DESCRIPTION OF THE INVENTION

Figure 2:
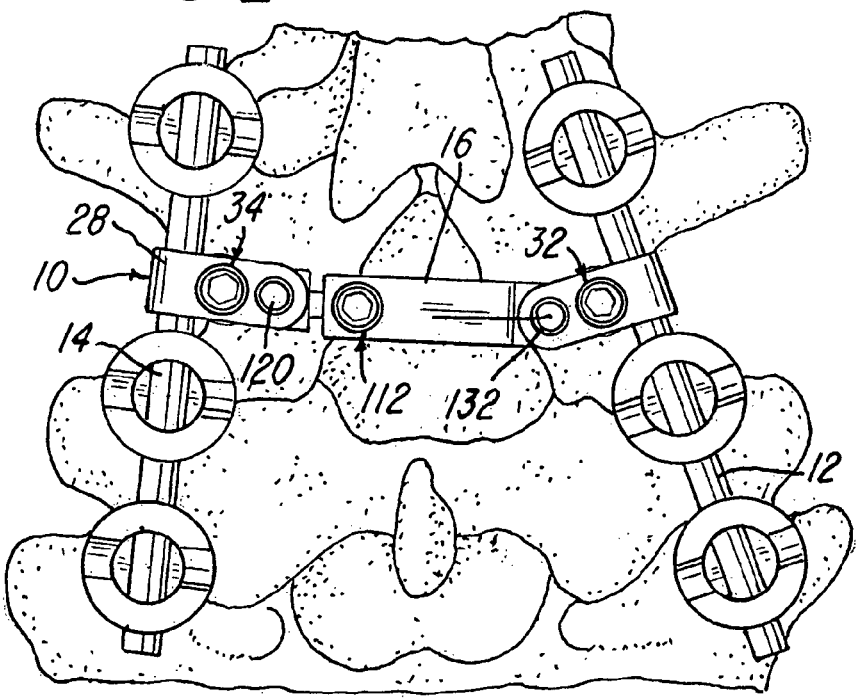
FIG. 2 is a partial elevation view of the cross connector apparatus depicted in FIG. 1 coupled to a pair of spaced spinal rods while positioned in an exemplary spinal environment.
Figure 1:
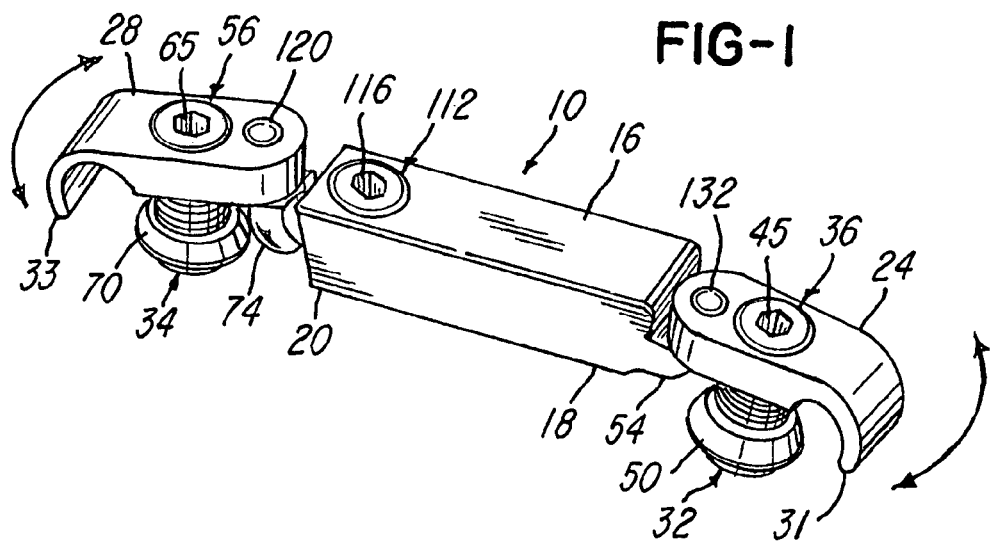
FIG. 1 is a perspective view of a cross connector apparatus for use with a spinal fixation system.

Referring now to the drawings in detail, wherein identical numerals indicate the same elements throughout the figures, FIG. 1 depicts a cross connector apparatus 10 utilized for retaining a pair of spinal rods 12 and 14 in spaced relation. It will be appreciated that spinal rods 12 and 14 (see FIG. 2) will generally be skewed in one or more planes with respect to each other in order to be placed in the proper position for a given person's spinal column.

More specifically, each cross connector apparatus 10 preferably includes a middle portion 16 having a first end 18, a second end 20, and a telescoping or extendable member 22 (FIG. 4) which is able to extend or telescope beyond second end 20 a predetermined amount. Further, a first side portion 24 is preferably positioned adjacent to first end 18 of middle portion 16, wherein first side portion 24 is rotatably coupled to middle portion 16 about an axis 21 (FIGS. 3 and 4) in at least a first plane defined by axes 23 and 25 (FIG. 4). A second side portion 28 is preferably positioned adjacent to second end 20 of middle portion 16, wherein second side portion 28 is rotatably coupled to extendable member 22 about an axis 26 in at least a second plane defined by axes 27 and 29 (see FIGS. 3 and 4). It will be seen that first and second side portions 24 and 28 preferably each include a curved portion 31 and 33, respectively, adapted, sized and shaped to conform with a portion of spinal rods 12 and 14. In addition, first and second side portions 24 and 28 preferably each include a mechanism 32 and 34, respectively, for both retaining the respective side portion in a desired position with respect to middle portion 16 and retaining one of spinal rods 12 and 14 thereto.

As best seen in FIGS. 3 and 4, retaining mechanism 32 of first side portion 24 preferably includes a cylindrical member 36 which is adjustably engagable with an opening 38 (FIG. 4) through first side portion 24. In a preferred embodiment, both cylindrical member 36 and an inner surface 40 of opening 38 include threads 42 and 44, respectively, so that cylindrical member 36 is able to move and be threadably receiving in and out of opening 38 as desired. A first generally cylindrical head or stop 46 is affixed to a first end 48 of cylindrical member 36 and acts as a stop for retaining a first ring member 50 thereon. A partial opening or socket 45 is provided in a second end 47 of cylindrical member 36 so that a corresponding or complementary-shaped tool may be utilized to rotate or screw cylindrical member 36.

The first ring member 50 is slidably received on cylindrical member 36 and is able to move along cylindrical member 36 so as to interface with the stop 46. The first ring member 50 also includes a wall 52 dimensioned and sized to be slightly larger than threads 42 which enables first ring member 50 to move up and down cylindrical member 36. It should be understood that the first ring member 50 is deformable and adapted to lock the rod 12 to the curved portion 31 and, substantially simultaneously, lock the first side portion 24 to the first end 18 of middle portion 16, as described herein. Thus, moving or screwing the cylindrical member 36 into and out of opening 38 a specified amount, it will be understood that first ring member 50 engages and substantially simultaneously disengages spinal rod 12 and a shoulder 54 (FIGS. 3 and 4) at first end 18 of middle portion 16 to lock these parts together.

Similarly, retaining mechanism 34 of second side portion 28 preferably includes a cylindrical member 56, which is adapted and operates similar to cylindrical member 36. The cylindrical member 56 is threaded which is adjustably threadable with an opening 58 through second side portion 28. In a preferred embodiment, both cylindrical member 56 and an inner surface 60 of opening 58 include threads 62 and 64, respectively, so that cylindrical member 56 is able to move and be threadably receiving in and out of opening 58 as desired. A second, generally cylindrical head or stop 66 is affixed to a first end 68 of cylindrical member 56 and acts as a stop for retaining a second ring member 70 thereon. A partial opening or socket 65 is provided in a second end 67 of cylindrical member 56 so that the corresponding or complementary-shaped tool may be utilized to rotate or screw cylindrical member 56 in the opening 58.

The second ring member 70 is slidaby received on cylindrical member 56 and is able to move along cylindrical member 56 so as to interface with the second head or stop 66. The second ring member 70 also includes a wall 72 dimensioned and sized to be slightly larger than threads 62 which enables second ring member 70 to move up and down cylindrical member 56. It should be understood that the ring 70 is deformable and adapted to lock the rod 14 to the curved portion 33 and, substantially simultaneously, lock the second side portion 28 to the second end 20 of middle portion 16. Thus, moving or screwing cylindrical member 56 into and out of opening 58 a specified amount, it will be understood that second ring member 70 engages and disengages spinal rod 14 and a shoulder 74 of extendable member 22 to lock these parts together.

Figure 6:
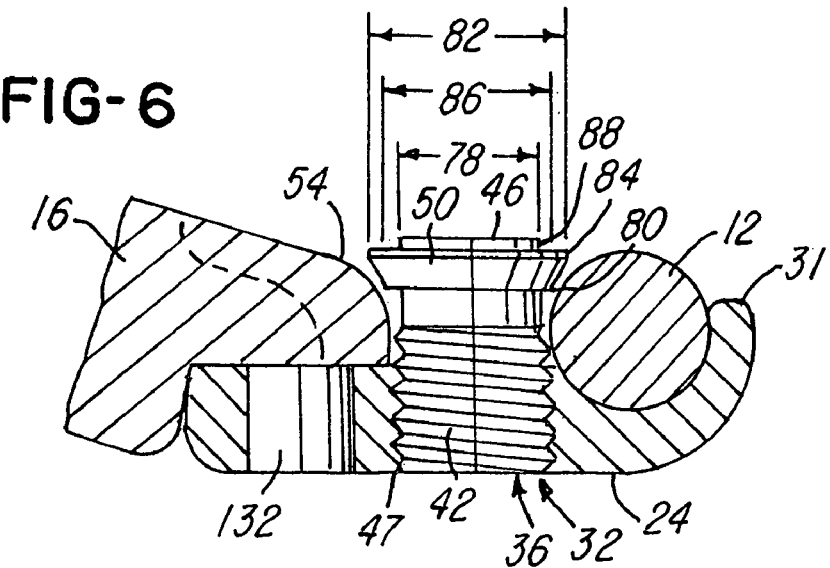
FIG. 6 is a partial section view of the cross connector apparatus depicted in FIGS. 1-5 taken along line 6-6 in FIG. 2.

Since retaining mechanisms 32 and 34 are essentially similar in configuration, first ring member 50 will be described more fully with the recognition that second ring member 70 conforms thereto. It will be appreciated that first ring member 50 (FIG. 3) is preferably substantially frusto-conical in shape. Thus, first ring member 50 includes the wall or inner surface 52 that has an inner diameter 87 (FIG. 3) and a first outer diameter 86 (FIG. 6) at a first end 80 and a second outer diameter 82 at a second end 84, where the diameter of first ring member 50 increases from first end 80 to second end 84, as shown. It should also be noted that a diameter 78 of an outer wall 88 of stop 46 is preferably greater than both the inner diameter 87 and the first outside diameter 86 of first ring member 50 so that first ring member 50 is retained on the cylindrical portion 36 and not able to pass thereover.

Figure 7:
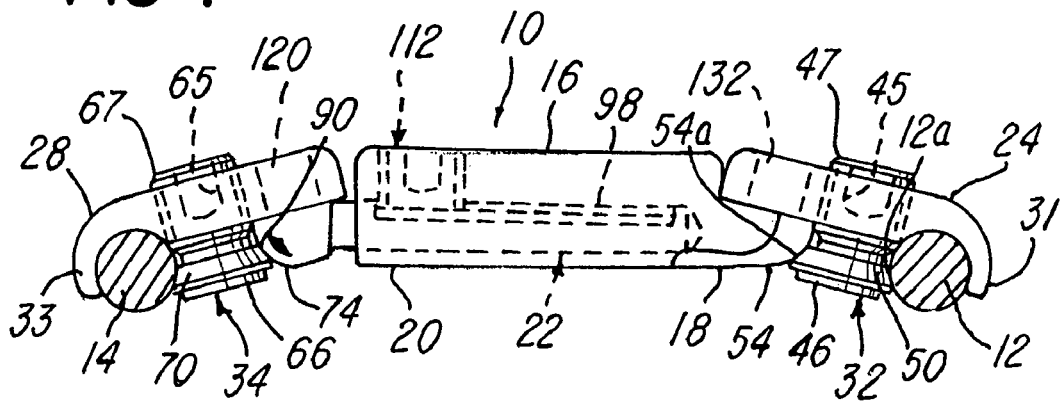
FIG. 7 is a top view of the cross connector apparatus depicted in FIGS. 1-6, where the side portions are locked in position and the spinal fixation rods are retained thereby.

In order to better enable first ring member 50 to engage and lock against both shoulder 54 of extendable member 22 and spinal rod 12 in a retained and locked manner, first ring member 50 is preferably made of a material having deformable properties, e.g., titanium, stainless steel, polymer, elastomer, alloy or composite. This enables first ring member 50 to better conform to a surface 54a (FIG. 7) of shoulder 54, as well as a portion 12a of spinal rod 12, when cylindrical member 36 of mechanism 32 is screwed or threaded into the opening 38.

It will be appreciated that extendable member 22 includes an elongated portion 98 (FIGS. 3 and 4) which telescopes, extends and is movable within a cavity 100 (FIG. 3) in middle portion 16. A first end 102 (FIG. 3) of elongated portion 98 resides within cavity 100 and shoulder 74 is located at a second end 104. Cavity 100 has the same approximate length as elongated portion 98 and is limited by the width of middle portion 16. A screw or cap 106 is provided for retaining and locking elongated portion 98 in a desired position to the middle portion 16. More specifically, a threaded opening 108 is preferably provided adjacent second end 20 of middle portion 16 from a front surface 110 thereof which communicates with cavity 100. The screw or cap 106 is rotatable within the threaded opening 108 so that it may engage elongated portion 98 at a first end of cylindrical member 112 and retain it in position. A partial opening or socket 116 is provided in a second end 118 of cylindrical member 112, where such socket 116 is configured so that a corresponding complementary-shaped tool may be utilized to move or screw the screw or cap 106 into and out of locking engagement with elongated portion 98.

Further, it will be seen that extendable member 22 includes a cylindrical member 120 (FIG. 3) extending from a front surface 122 of second end 104. Cylindrical member 120 is sized so as to fit within a second opening 124 in second side portion 28. In this way, second side portion 28 is rotatably coupled to extendable member 22 and, therefore, to middle portion 16 as described above.

It will also be understood from FIGS. 10-15 that elongated portion 98 may be rotatable about a longitudinal axis 103 substantially aligned with axis 27 and in a third plane defined by axes 26 and 29 which is generally perpendicular to the second plane defined by axes 27 and 29 as identified herein. As seen, second end 104 (FIG. 3) has a pair of surfaces 128 and 130 (FIG. 15) with a reduced radius, which permits elongated portion 98 to rotate within shoulder 74 (FIG. 3). It is preferred that elongated portion 98, and therefore second side portion 28, be rotatable in either the clockwise or counterclockwise direction by a predetermined number of degrees, such as approximately ±90 degrees.

Figure 5:
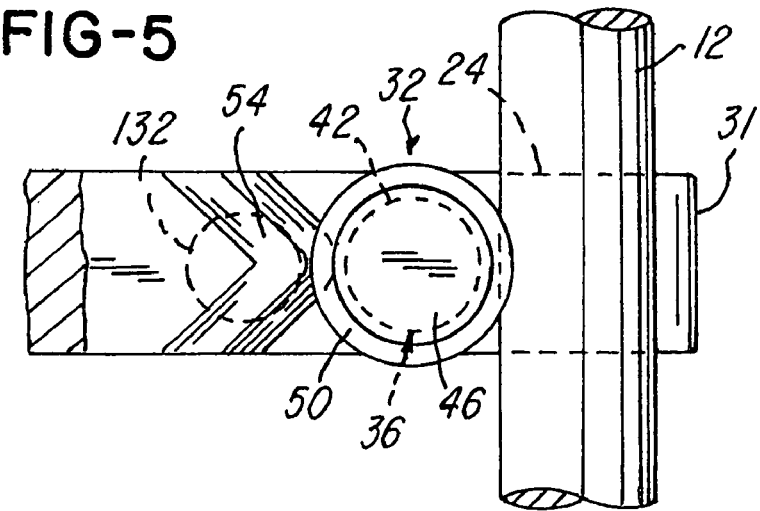
FIG. 5 is a partial rear view of the cross connector apparatus depicted in FIGS. 14.
Figure 8:
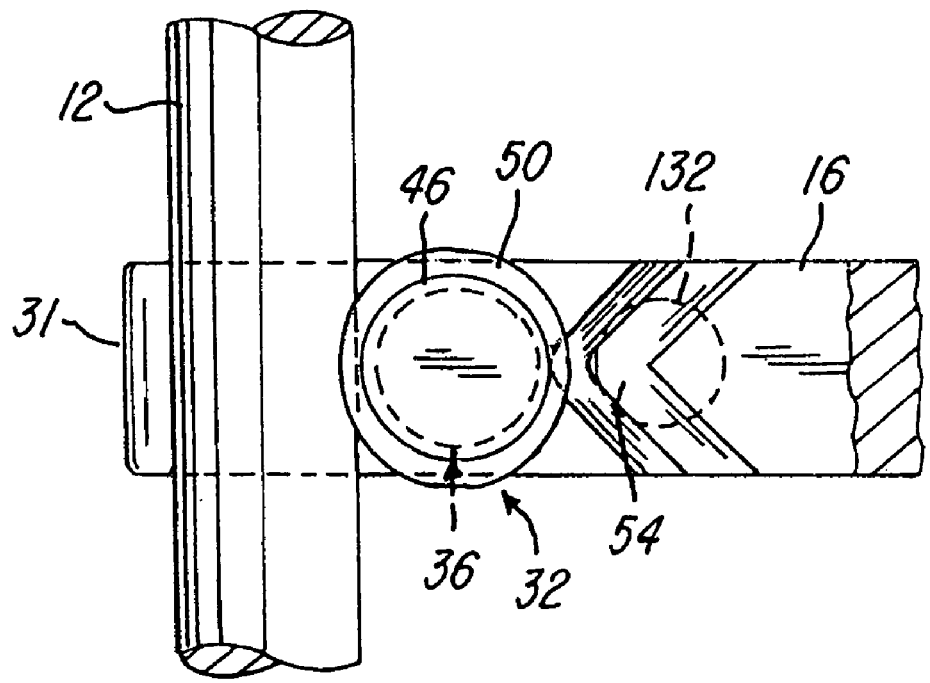
FIG. 8 is a partial rear view of the cross connector apparatus depicted in FIGS. 14.
Figure 9:
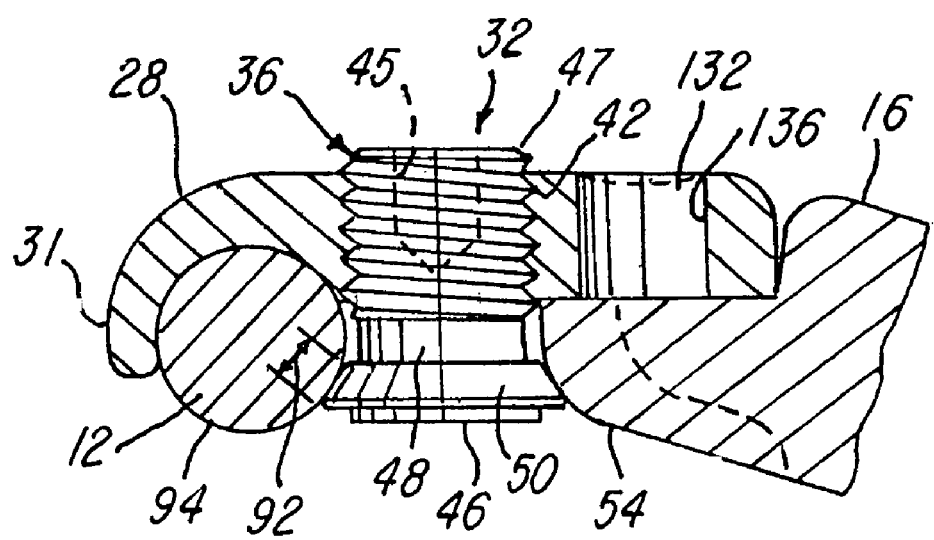
FIG. 9 is a partial section view of the cross connector apparatus depicted in FIGS. 1-4 and 8.

It will also be seen that middle portion 16 preferably includes a cylindrical post or member 132 (FIG. 3) extending from a front surface 111 of shoulder 54 (FIGS. 5, 8 and 9) adjacent first end 18 of middle portion 16. Cylindrical member 132 is adapted and sized to fit within a second opening 136 in first side portion 24. In this way, the first side portion 24 is rotatably coupled to middle portion 16.

It will be appreciated that mechanisms 32 and 34, respectively, function to retain and lock first and second sides portions 24 and 28 to the middle portion 16, as well as spinal rods 12 and 14, substantially simultaneously. This permits adjustments of the relative positions in a simple and efficient manner.

Advantageously, the use of the deformable rings 50 and 70 permits the simultaneous locking of the rod relative to the first and second side portions 24 and 28, while locking the first and second side portions 24 and 28 to the middle portion 16.

During use, the surgeon will generally attach spinal rods 12 and 14 in position first. In order to assist in the stability of rods 12 and 14, cross connector apparatus 10 is first positioned so that spinal rod 12 is aligned within curved portion 31. First side portion 24 is permitted to rotate with respect to middle portion 16 via the coupling provided by cylindrical post 132 within second opening 136 in first side portion. In this way, cross connector apparatus 10 is able to adjust to the stationary position of spinal rod 12. Spinal rod 12 and first side portion 24 are then locked in such position by utilizing retaining mechanism 32. More specifically, cylindrical member 36 is rotated into opening 38 until first ring member 50 engages a portion 12a of spinal rod 12 and shoulder 54, whereupon ring member 50 is deformed to provide the locking action.

Once cross connector apparatus 10 is positioned with respect to spinal rod 12, extendable member 22 is extended from middle portion 16 an amount so that curved portion 33 of second side portion 28 is aligned with spinal rod 14. It will be understood that extendable member 22 may be rotated about its axis 103 to provide an adjustment in a transverse plane, whereby spinal rod 14 is better accommodated. Once spinal rod 14 is in position, and second side portion 28 is rotated as necessary about cylindrical member 120 of extendable member 22, retaining mechanism 34 is activated to lock spinal rod 14 and second side portion 28 in position. In particular, cylindrical member 56 is rotated into opening 58 of second side portion 28 until second ring member 70 engages a portion of spinal rod 14 and a portion of shoulder 74 on extendable member 22.

Having shown and described the preferred embodiment of the present invention, further adaptations of the cross connector apparatus, as well as the mechanisms 32 and 34 for retaining first and second side portions 24 and 28, respectively, in position with respect to middle portion 16 and retaining spinal rods 12 and 14, can be accomplished by appropriate modifications by one of ordinary skill in the art without departing from the scope of the invention. Moreover, it will be understood that mechanism 32 and 34 described herein may be utilized with other cross connector configurations not depicted herein.

What is claimed is:

1. A cross connector apparatus for retaining a pair of spinal rods in spaced relation, comprising:
a middle portion having a first end, a second end, and an extendable member which is able to extend beyond said second end a specified amount;
a first side portion positioned adjacent to said first end of said middle portion, wherein said first side portion is rotatably or pivotally coupled to said middle portion in at least a first plane; and
a second side portion positioned adjacent to said second end of said middle portion, wherein said second side portion is rotatably or pivotally coupled to said extendable member in at least a second plane;
at least one of said first side portion or said second side portion comprising a retaining mechanism for retaining said at least one of said first side portion or said second side portion, respectively, in a fixed or locked position with respect to said middle portion and substantially simultaneously retaining a spinal rod member in a locked position in said at least one of said first side portion or said second side portion:
said retaining mechanism comprising at least one deformable member situated on a tightening member, said at least one deformable member being deformable so that when said tightening member is tightened, said at least one deformable member at least partially deforms against at least one of said spinal rod member, said first side portion or second side portion, and substantially simultaneously cause said at least one of said first side portion or said second side portion to become fixed or locked relative to said middle portion.

2. The cross connector apparatus of claim 1, said retaining mechanism of said first side portion further comprising:
   (a) a cylindrical member which is adjustably engagable with an opening through said first side portion;
   (b) a stop affixed to a first end of said cylindrical member; and
   (c) a first ring member adjustably engagable with said cylindrical member, wherein said first ring member is able to move along said cylindrical member so as to interface with said stop;
   wherein said cylindrical member is able to move into and out of said opening so that said first ring member engages and disengages said spinal rod member and a shoulder at said first end of said middle portion.

3. The cross connector apparatus of claim 2, wherein said first ring member is substantially frusto-conical in shape.

4. The cross connector apparatus of claim 2, wherein said first ring member is deformable.

5. The cross connector apparatus of claim 2, said cylindrical member including a partial opening through a second end thereof shaped so as to be engaged by a specified tool.

6. The cross connector apparatus of claim 2, wherein an inner diameter of said first ring member is less than an outer diameter of said stop.

7. The cross connector apparatus of claim 1, said retaining mechanism of said second side portion further comprising:
   (a) a cylindrical member adjustably engagable with an opening through said second side portion;
   (b) a stop affixed to a first end of said cylindrical member; and
   (c) a second ring member adjustably engagable with said cylindrical member, wherein said second ring member is able to move along said cylindrical member so as to interface with said stop;
   wherein said cylindrical member is able to move into and out of said opening so that said second ring member engages and disengages said spinal rod member and a shoulder of said extendable member.

8. The cross connector apparatus of claim 7, wherein said second ring member is substantially frusto-conical in shape.

9. The cross connector apparatus of claim 7, wherein said second ring member is deformable.

10. The cross connector apparatus of claim 7, said cylindrical member including a partial opening through a second end thereof shaped so as to be engaged by a specified tool.

11. The cross connector apparatus of claim 7, wherein an inner diameter of said second ring member is less than an outer diameter of said stop.

12. The cross connector apparatus of claim 1, said first side portion and said second side portion each including a curved portion sized and shaped to conform with a portion of a spinal rod.

13. The cross connector apparatus of claim 7, wherein said extendable member is rotatable within said shoulder thereof a specified amount in a third plane substantially perpendicular to said second plane.

14. The cross connector apparatus of claim 13, wherein said extendable member is able to rotate within said third plane in a range of approximately 45° to approximately −45°.

15. The cross connector apparatus of claim 7, further comprising a mechanism for retaining said extendable member in a desired position.

16. The cross connector apparatus of claim 2, said middle portion further comprising a cylindrical member extending from a surface of said shoulder at said first end, wherein said cylindrical member interfaces with a second opening in said first side portion so as to be rotatably coupled thereto.

17. The cross connector apparatus of claim 7, said extendable member further comprising a cylindrical member extending from a surface of said shoulder, wherein said cylindrical member interfaces with a second opening in said second side portion so as to be rotatably coupled thereto.

18. A process for retaining a pair of spinal rods in spaced relation, comprising the following steps:
   (a) retaining a first spinal rod to a first side portion of a cross connector apparatus with a first retainer;
   (b) retaining said first side portion of said cross connector apparatus in a locked position with said first retainer;
   (c) moving a second side portion of said cross connector apparatus coupled to said first side portion a specified distance from said first side portion thereof;
   (d) retaining a second spinal rod to said second side portion of said cross connector apparatus using a second retainer; and
   (e) retaining said second side portion of said cross connector apparatus in a locked position with said second retainer;
   wherein said at least one of said first retainer or said second retainer is a deformable member, said deformable member at least partially deforming in response to tightening said deformable member substantially simultaneously to lock either said first spinal rod to said first side portion and substantially simultaneously locking movement said first side portion. or of said second retainer, lock said second spinal rod to said second side portion while substantially simultaneously locking movement said second side portion,
   said retaining functions of steps (a) and (b) occur substantially simultaneously and said retaining functions of steps (d) and (e) occur substantially simultaneously.

19. The process of claim 18 wherein at least one of said first retainer or said second retainer is a deformable ring.

20. The process of claim 18 wherein each of said first and second retainer comprises a deformable ring.

* * * * *

UNITED STATES PATENT AND TRADEMARK OFFICE
CERTIFICATE OF CORRECTION

PATENT NO. : 7,922,747 B2  
APPLICATION NO. : 11/873452  
DATED : April 12, 2011  
INVENTOR(S) : David Louis Kirschman Page 1 of 1

It is certified that error appears in the above-identified patent and that said Letters Patent is hereby corrected as shown below:

In Column 2, Line 61, please delete "14" and insert -- 1- 4 -- therefor.

In Column 3, Line 2, please delete "14" and insert -- 1- 4 -- therefor.

Signed and Sealed this  
Thirteenth Day of March, 2012

David J. Kappos  
*Director of the United States Patent and Trademark Office*